(12) United States Patent
Ravkin et al.

(10) Patent No.: US 7,381,375 B2
(45) Date of Patent: Jun. 3, 2008

(54) ASSAY SYSTEMS WITH ADJUSTABLE FLUID COMMUNICATION

(75) Inventors: Ilya Ravkin, Palo Alto, CA (US); Oren E. Beske, Sunnyvale, CA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 11/175,992

(22) Filed: Jul. 5, 2005

(65) Prior Publication Data

US 2006/0013031 A1 Jan. 19, 2006

Related U.S. Application Data

(63) Continuation-in-part of application No. 10/282,940, filed on Oct. 28, 2002.

(60) Provisional application No. 60/585,150, filed on Jul. 2, 2004, provisional application No. 60/421,280, filed on Oct. 25, 2002, provisional application No. 60/348,027, filed on Oct. 26, 2001.

(51) Int. Cl.
*B01L 3/00* (2006.01)

(52) U.S. Cl. .................. 422/102; 422/68.1; 435/283.1; 435/287.1; 435/288.3; 435/288.4

(58) Field of Classification Search .................. 422/67, 422/68.1, 102; 435/283.1, 287.1, 288.3, 435/288.4
See application file for complete search history.

(56) References Cited

U.S. PATENT DOCUMENTS

| | | | |
|---|---|---|---|
| 4,053,362 A | 10/1977 | Sforza | |
| 4,980,293 A | 12/1990 | Jeffs | |
| 5,120,503 A | 6/1992 | Hinckley et al. | |
| 5,130,105 A | 7/1992 | Carter et al. | |
| 5,134,064 A | 7/1992 | Nordlund | |
| 5,141,718 A | 8/1992 | Clark | |
| 5,593,875 A | 1/1997 | Wurm et al. | |
| 5,830,411 A | 11/1998 | Martinell Gisper-Sauch | |
| 5,916,526 A | 6/1999 | Robbins | |
| 5,928,934 A | 7/1999 | McCormick | |
| 5,989,835 A | 11/1999 | Dunlay et al. | |
| 6,027,695 A | 2/2000 | Oldenburg et al. | |
| 6,039,804 A * | 3/2000 | Kim et al. .................. 117/206 |
| 6,168,914 B1 | 1/2001 | Campbell et al. | |
| 6,232,066 B1 | 5/2001 | Felder et al. | |
| 6,238,869 B1 | 5/2001 | Kris et al. | |
| 6,306,975 B1 | 10/2001 | Zhao et al. | |
| 6,406,845 B1 | 6/2002 | Walt et al. | |
| 6,413,776 B1 | 7/2002 | Vogels et al. | |
| 6,429,027 B1 * | 8/2002 | Chee et al. .................. 436/518 |
| 6,458,533 B1 | 10/2002 | Felder et al. | |
| 6,699,665 B1 * | 3/2004 | Kim et al. ..................... 435/6 |
| 6,913,732 B2 | 7/2005 | Sha et al. | |

FOREIGN PATENT DOCUMENTS

| | | | |
|---|---|---|---|
| JP | 1-144970 | | 6/1989 |
| WO | WO 98/50782 | | 11/1998 |
| WO | WO 00/63419 | | 10/2000 |
| WO | WO 02/37944 | | 5/2002 |
| WO | WO 02/48676 | * | 6/2002 |
| WO | WO 03/036265 | | 5/2003 |

OTHER PUBLICATIONS

*A New Technology Platform for Drug Discovery*, Glezer et al., Meso Scale Discovery, pp. 1-9, undated.
*Arrays of Arrays for High-Throughput Gene Expression Profiling*, Zarrinkar et al., Genome Research, vol. 11, No. 7, pp. 1256-1261, Jul. 2001.
*Membrane Array Technology for Drug Discovery*, Groves, Current opinion in Drug Discovery &Development, vol. 5, No. 4, pp. 606-612, 2002.
*Microtiter Format for Simultaneous Multianalyte Detection and Development of a PCR-Chemiluminescent Enzyme Immunoassay for Typing Human Papillomavirus DNAs*, Roda et al.,Clinical Chemistry, vol. 48, No. 10, pp. 1654-1660, Oct. 2002.
*SearchLight™ Protein Array Technology*, Pierce Boston Technology Center, internet pp. 1-2, printed Oct. 21, 2002.
Martel, R. R., et al., "Multiplexed Chemiluminescent Assays in ArrayPlates™ for High-Throughput Measurement of Gene Expression," *Biomedical Nanotechnology Architectures and Applications*, 4626:35-43 (2002).
Zhao, X., et al., "Ultra-High Throughput SNP Genotyping for Pharmacogenetics and Drug Discovery," Orchid Biosciences, Inc., 2 pages, presented at HGM2002 (Apr. 2002).

\* cited by examiner

*Primary Examiner*—Long V. Le
*Assistant Examiner*—Jacob Cheu
(74) *Attorney, Agent, or Firm*—Hamilton, Brook, Smith & Reynolds, P.C.

(57) ABSTRACT

Systems, including apparatus and methods, for performing assays with adjustable fluid communication between samples.

11 Claims, 7 Drawing Sheets

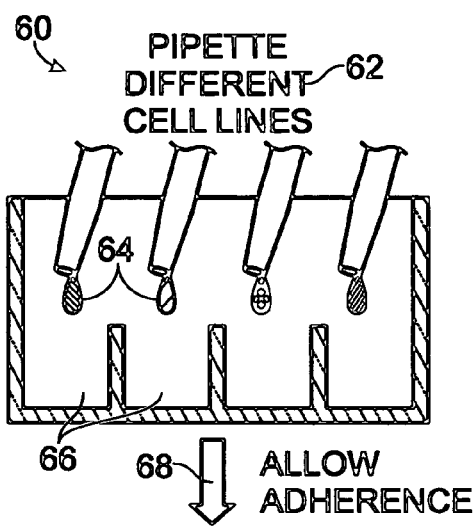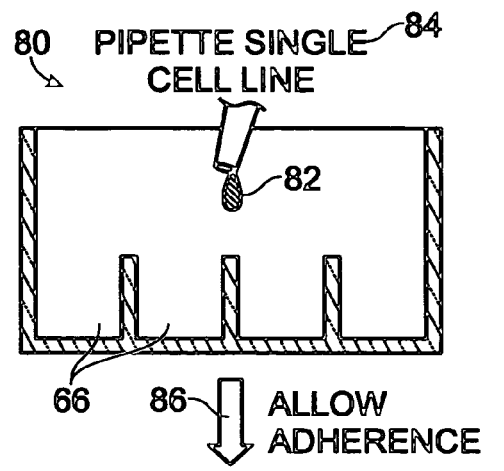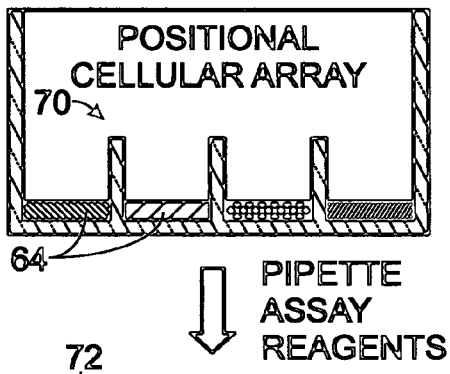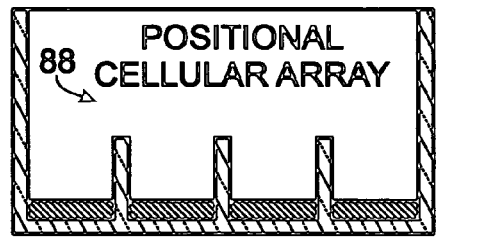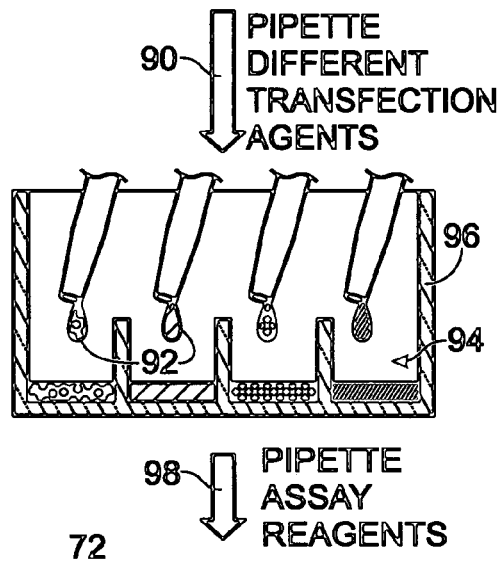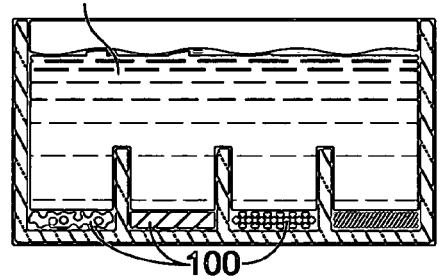

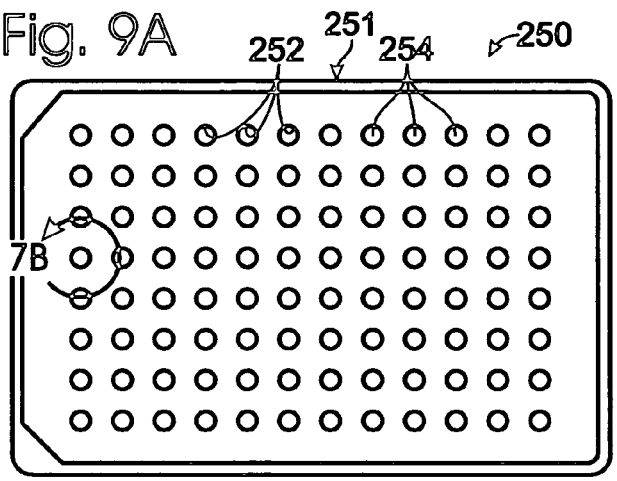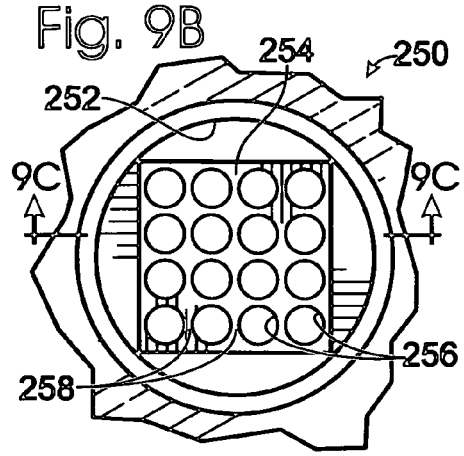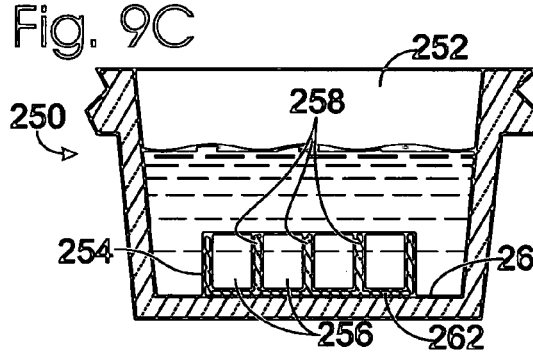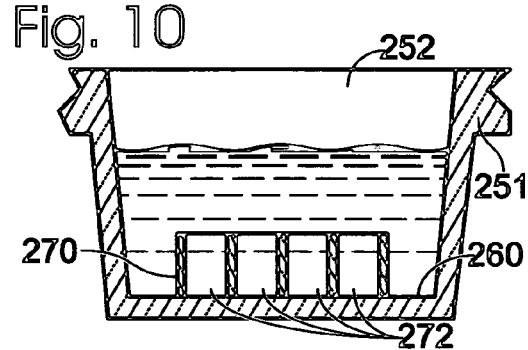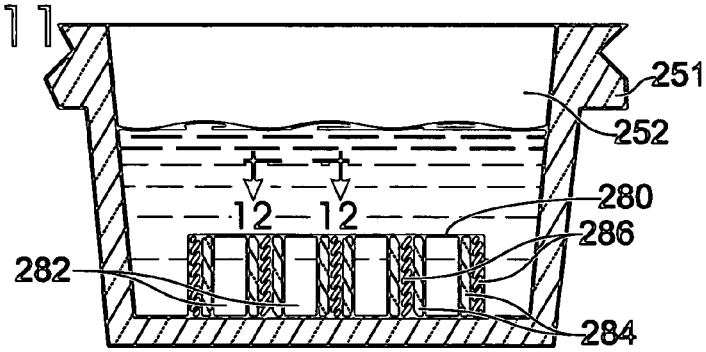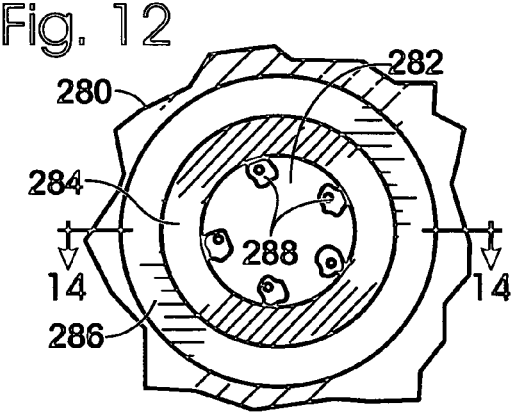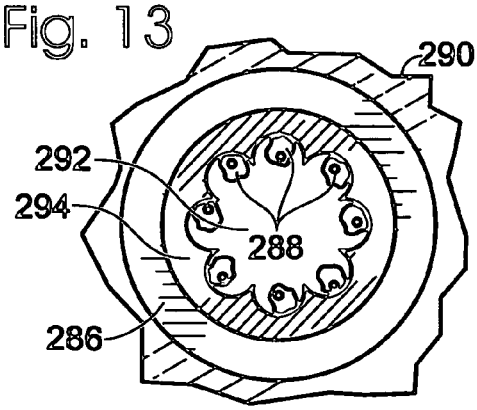

ASSAY SYSTEMS WITH ADJUSTABLE FLUID COMMUNICATION

CROSS-REFERENCES TO PRIORITY APPLICATIONS

This application is a continuation-in-part of U.S. patent application Ser. No. 10/282,940, filed Oct. 28, 2002. This application also claims the benefit under 35 U.S.C. § 119(e) of U.S. Provisional Patent Application Ser. No. 60/585,150, filed Jul. 2, 2004.

U.S. patent application Ser. No. 10/282,940 claims the benefit under 35 U.S.C. § 119(e) of the following U.S. provisional patent applications Ser. No. 60/348,027, filed Oct. 26, 2001; and Ser. No. 60/421,280, filed Oct. 25, 2002.

The above-identified U.S. and provisional patent applications are all incorporated herein by reference in their entirety for all purposes.

CROSS-REFERENCES TO RELATED APPLICATIONS

This application incorporates by reference in their entirety for all purposes the following U.S. patent applications Ser. No. 09/549,970, filed Apr. 14, 2000; Ser. No. 09/694,077, filed Oct. 19, 2000; Ser. No. 10/120,900, filed Apr. 10, 2002; Ser. No. 10/238,914, filed Sep. 9, 2002; Ser. No. 10/273,605, filed Oct. 18, 2002; Ser. No. 10/282,904, filed Oct. 28, 2002; Ser. No. 10/382,796, filed Mar. 5, 2003; Ser. No. 10/382,797, filed Mar. 5, 2003; Ser. No. 10/382,818, filed Mar. 5, 2003; Ser. No. 10/407,630, filed Apr. 4, 2003; Ser. No. 10/444,573, filed May 23, 2003; Ser. No. 10/445,291, filed May 23, 2003; Ser. No. 10/713,866, filed Nov. 14, 2003; Ser. No. 10/842,954, filed May 10, 2004; Ser. No. 10/901,942, filed Jul. 28, 2004; Ser. No. 10/942,322, filed Sep. 15, 2004; Ser. No. 10/942,323, filed Sep. 15, 2004; and Ser. No. 11/039,077, filed Jan. 18,2005.

This application also incorporates by reference in its entirety for all purposes the following U.S. provisional patent application Ser. No. 60/672,580, filed Apr. 18, 2005.

INTRODUCTION

Modern laboratory techniques such as cell phenotyping, microscale chemical syntheses, and high-throughput screening of candidate drug compounds often require the preparation and analysis of hundreds of thousands or millions of samples. This preparation and analysis may be facilitated by packaging samples together in two-dimensional multi-well sample holders such as microplates for rapid or simultaneous processing in an automated device.

Microplates generally comprise sample holders having a frame and a plurality of individual sample wells disposed in the frame for holding a corresponding number of samples. Microplates may be rectangular in shape, with cylindrical, hexahedral, or frustoconical wells arranged in pre-defined arrays (for example, rectangular or other geometric arrays), enabling the sample holder to be used with standard microplate equipment, such as handlers, washers, and/or readers, among others. Each sample well is essentially a small container that may hold an individual sample in fluid isolation from the samples in other wells in the microplate. Such samples may include but are not limited to biological cells or chemical agents.

Standard microplates may have a number of shortcomings because of the fluid isolation of their wells. For example, it is in practice difficult or impossible to guarantee identical testing conditions between different samples in different wells. In particular, the concentration of reagent within the reagent fluid, the volume (height) of reagent fluid (and thus the pressure and the rate of exchange of material with the environment at the bottom of the sample well), the temperature, and/or other physical properties of reagent fluid may vary in an unknown fashion from well to well. This variation may lead to errors in sample analysis, causing misinterpretation of the results and necessitating further sample testing. Furthermore, dispensing reagents to standard microplates can be quite inefficient. Sample wells are addressed individually during reagent addition, even when the same reagent is added to each well.

SUMMARY

The present teachings provide systems, including apparatus and methods, for performing assays with adjustable fluid communication between samples.

BRIEF DESCRIPTION OF THE DRAWINGS

FIG. 4 is a pair of flowcharts showing exemplary methods for forming and assaying a cell array in a subdivided sample well, in accordance with aspects of the present teachings.

FIG. 9A is a top plan view of an exemplary microplate having wells subdivided by exemplary subarray inserts disposed in the wells, in accordance with aspects of the present teachings.

FIG. 9B is an enlarged view of one of the wells and subarray inserts of FIG. 9A.

FIG. 9C is a sectional view of the well and subarray insert of FIG. 9B, taken generally along line 9C-9C of FIG. 9B, with the subarray insert defining a plurality of sub-wells.

FIG. 10 is a sectional view of an alternative embodiment of the subarray insert of FIGS. 9A-C, with the subarray insert defining a plurality of apertures, in accordance with aspects of the present teachings.

FIG. 11 is a sectional view of another embodiment of a subarray insert, with the subarray insert defining a plurality of apertures, each of which is surrounded by a transmissive sleeve and an optical cladding, in accordance with aspects of the present teachings.

FIG. 12 is a fragmentary plan view of the subarray insert of FIG. 11, viewed generally along line 12-12 of FIG. 11 and showing one of the apertures and its associated sleeve and cladding, in accordance with aspects of the present teachings.

FIG. 13 is a fragmentary plan view of an alternative embodiment of an aperture and its associated sleeve and cladding, in accordance with aspects of the present teachings.

DETAILED DESCRIPTION

Figure 1:
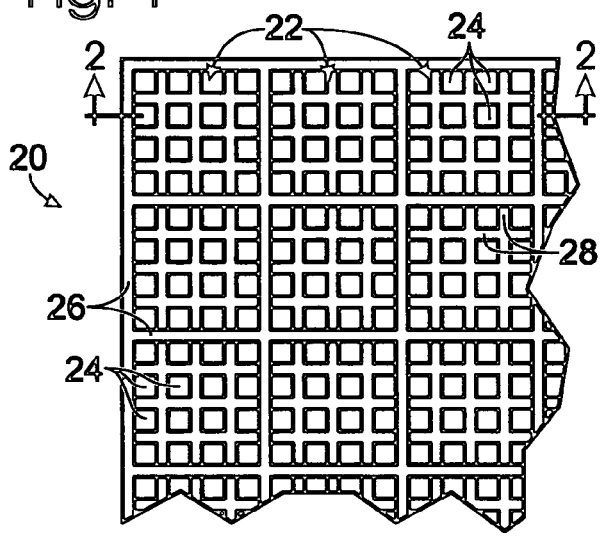
FIG. 1 is a fragmentary top plan view of a sample holder with a two-tiered hierarchy of sample compartments in which individual wells are subdivided into sub-wells, in accordance with aspects of the present teachings.

The present teachings provide systems, including apparatus and methods, for performing assays with adjustable fluid communication between samples. The apparatus may provide an array of identifiable subarrays. The array may be a positional array, produced by an array-defining device or frame, such as a microplate. At each array position (e.g., each well of a microplate), a subarray may be produced by a plurality of sub-compartments. The sub-compartments may be defined by holes, that is, sub-wells (recesses) or apertures (through-holes or capillaries) separated by inner walls within each subarray. The inner walls may be lower in height than an outer wall that surrounds each subarray. In some examples, the inner walls may extend to different heights to form at least a two-level (or more) hierarchy of sub-wells within a well. For example, the sub-wells in a well may be arranged to be addressable with fluid (1) individually, (2) as separate sub-groups (such as sub-groups disposed in rows or columns within the well), and/or (3) together as a complete group in the well. The outer walls may correspond to the walls of the wells within which each subarray is disposed.

In one embodiment the device for assaying a plurality of biological or chemical samples, comprising: a frame; and a plurality of wells disposed in the frame and addressable individually with fluid, each well including a plurality of sub-wells addressable with fluid either (a) individually, or (b) as two or more groups, wherein each well has an outer wall and at least two inner walls of lower height than the outer wall and different in height from each other, and wherein the at least two inner walls extend to different heights to form at least two levels, thereby dividing the well into the sub-wells and the two or more groups of sub-wells.

The sub-wells or apertures may be formed integrally with the wells, for example, integral to a microplate, or may be formed separately as subarray holders or subarray inserts to be placed in the wells. Alternatively, the subarray holders or inserts may provide both the wells and the sub-wells or apertures, that is, both the inner and outer walls. Accordingly, such subarray holders may be removably disposed in any suitable frame at which positions of the subarray holders are defined and thus the holders identified. In some embodiments, the subarray holders may be identifiable independent of position, for example, through an identifying code included in each holder. Accordingly, subarray holders may be disposed in positionally flexible (nonpositional) arrays in any suitable container or containers.

The methods comprise techniques for performing assays in which samples may be brought into or out of fluid communication with each other by adjusting the amount or level of fluid reagent in each sample well. As a result, sub-wells or apertures within a subarray may be addressed with fluid individually or as a group, or, in some cases, as sub-groups. In some embodiments, the samples may be a plurality of different cell types disposed in different rows (or columns) within each subarray. For example, the cell types may be delivered to individual sub-wells in smaller volumes of fluid that allow fluid isolation of the sub-wells of the subarray. Also using such smaller volumes, the cells in each sub-well may be addressed individually with different reagents. For example, different transfection materials may be introduced to distinctly modify the cells in different sub-wells. Using a larger volume of fluid to raise the fluid level and thus place portions of the subarray in fluid communication, the cell types/populations of a subarray may be addressed as a group with a single reagent, such as a candidate cell modulator (for example, a drug candidate). Accordingly, different subarrays within an array may be addressed with different reagents. In some embodiments, cell types and reagents exposed to the cell types may be identified by position with the subarray and within the array.

The present teachings thus provide systems for simultaneously exposing multiple biological and/or chemical samples to a continuous fluid reagent environment, allowing experiments in which a plurality of samples is exposed to identical testing conditions. These systems may increase the number of samples that can be tested in a given time, may reduce the number of fluid transfer operations needed to perform a given number of experiments, and/or may reduce experimental uncertainties associated with possible variations in fluid reagent environment across multiple samples.

The present teachings also provide systems for exposing samples sequentially to different fluid reagents and to the same reagent, in a multi-step process performed in any suitable order. These systems may increase the rate at which samples may be tested, while reducing experimental uncertainties associated with the preparation of identical samples and/or possible variations in fluid reagent environment across multiple samples.

In one embodiment, the device for assaying a plurality of biological or chemical samples, comprising:
a frame;
a plurality of wells disposed in the frame and addressable individually with fluid;

a set of sub-wells disposed in each well and addressable individually or as a group by adjusting fluid levels, wherein the heights of the sub-wells are lower than that of said wells; and a set of relatively smaller sub-wells disposed in each sub-well and addressable individually or as a group by adjusting fluid levels, wherein the height of each relatively smaller sub-well is lower than that of sub-wells.

Further aspects of the present teachings are described below, in the following sections: (I) apparatus, including (A) microplates with integral subdivided wells, (B) subarray inserts, and (C) manufacture of microplates and subarray inserts; (II) assay methods, including (A) arraying samples and/or reagents using subdivided microplates, and (B) assays with adjustable fluid communication; (III) detection systems; and (IV) examples.

I. APPARATUS

The present teachings provides apparatus for holding samples in subarrays so that the samples are addressable with fluid individually, as a set of sub-groups, and/or as a group. The subarrays may be defined by sample wells divided into sub-wells (or apertures) by inner walls, where the inner walls (or portions thereof) may be lower in height than the outer walls of the well. Such an arrangement of wells and sub-wells may be referred to generically as a superpositional array of sample wells. In a superpositional array, information about samples and reagents may be determined based on position within the subarray and identification of the subarray, for example, by its position within the array. One preferred form of the apparatus includes an industry-standard microplate, such as those detailed below, where each sample well in the microplate is divided into sub-wells, and where one or more of the inner walls in one or more of the sample wells is lower in height than the outer walls of the corresponding well. In other embodiments, the apparatus includes a removable subarray insert defining plural apertures or sub-wells. One or plural arrays may formed with the subarray inserts and used separately, for example, in different wells of a microplate, or as a mixture in any suitable container. Alternatively, the removable subarray inserts may also include outer walls, so that each insert defines both a well and sub-wells that divide the well. Such subarray inserts may be disposed in any suitable array-defining frame. These and other aspects of the present teachings are described below, including (A) microplates with integral subdivided wells, (B) subarray inserts, and (C) manufacture of microplates and subarray inserts.

A. Microplates with Integral Subdivided Wells

Figure 2:
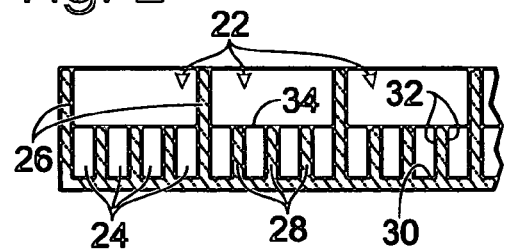
FIG. 2 is a sectional view of the sample holder of FIG. 1, taken generally along line 2-2 of FIG. 1, in accordance with aspects of the present teachings.

FIGS. 1 and 2 show top plan and sectional views, respectively, of a sample holder or microplate 20 having a hierarchy of wells 22 and sub-wells 24 within each well. Each well 22 is surrounded by an outer wall 26 and subdivided into sub-wells 24 using inner walls or dividers 28 that partition the well into the sub-wells. Each sub-well 24 is configured to hold a sample independently, for example, cells attached to a bottom surface 30 or a side surface 32 of the sub-well, or a sample in suspension or solution held in a volume defined by the sub-well. Inner walls 28 may be lower than outer walls 26 of the well, so that sub-wells 24 may exist either in a state of fluid isolation (when the sample well is only slightly filled, or at least below sub-well top 34) or in a state of fluid communication (when the sample well is nearly filled, or above top 34), as shown in FIG. 2.

The wells may have any suitable shape(s) and/or size(s). When viewed from the side and/or in vertical cross-section, the outer walls may be straight (that is, vertical or angled), curved (for example, parabolic, circular, or arcuate), or a combination thereof. For example, FIGS. 1 and 2 show wells 22 that are straight when viewed from above or from the side. When viewed from the top and/or in horizontal cross section, wells may have outer walls that are polyhedral, oval, curvilinear, and/or the like. For example, FIG. 1 shows wells that are square when viewed from above. Wells may be configured to hold any suitable volume of fluid, including less than about 2 mL, 1 mL, 0.5 mL, or 0.1 mL, among others.

The sub-wells of a well (and/or subarray insert) also may have any suitable shape(s) and/or size(s). These shapes may be as described above for wells. For example, FIGS. 1 and 2 show sub-wells 24 that are square when viewed from above and rectangular when viewed from the side. The shapes of the sub-wells may be similar or different within a well, and the shape(s) of the sub-wells may be similar to or distinct from the shape of the well. Sub-wells may have any suitable depth(s). For example, sub-wells may be formed as deep (elongate), intermediate-depth, and/or shallow recesses. Accordingly, sub-wells within one well or carried in different wells may hold similar or different volumes of fluid. Sub-wells generally hold substantially less liquid than the well in which they are carried. Accordingly, sub-wells may be configured to hold less than about 10 µL, 1 µL, 100 nL, or 10 nL of fluid, among others. In exemplary embodiments, sub-wells hold about 2-4 µL of fluid.

A subdivided well generally may include any suitable number of sub-wells, in any suitable geometrical arrangement, based on the overall size of the well, the size of individual sub-wells, the spacing between sub-wells (generally, inner wall thickness), the desired number of samples per well, and/or the like. For example, sub-wells may be arranged in a rectangular configuration (to form rows and columns of sub-wells within a well), as shown in FIG. 1, or a circular, staggered, or irregular configuration, among others, either in a defined or arbitrary orientation relative to the well and the microplate. The arrangement may be symmetrical or asymmetrical. An asymmetrical configuration may be used, for example, to allow identification of sub-wells that may not have a defined and/or fixed orientation relative to the microplate (for example, subarray inserts described below in part B of this section).

In contrast to the embodiment shown in FIG. 1, other embodiments may have inner walls of two or more different heights within a well to form a multi-level hierarchy for addressing sub-wells with fluid. For example, individual sub-wells in a well may be separated by an inner wall(s) of a first height, groups of sub-wells by an inner wall(s) of a second, greater height, and the entire well by an outer wall(s) of greatest height. In this case, individual sub-wells, groups of sub-wells, or all sub-wells of the well may be addressed with samples and/or reagents based on the volume/level of fluid in the well and/or in each sub-well.

Sub-wells may include features to control mixing and/or fluid entry from the region of the well disposed above the sub-well. For example, a sub-well may include a lip (or ledge) or hydrophobic ring disposed near the top of the sub-well. The lip may be a substantially orthogonal projection from the side walls of the sub-well to form a narrowed sub-well opening or mouth to receive fluid. Further aspects of sub-wells that may be included in microplates are described below in part B of this section and in Section IV, particularly Examples 1, 3, 4, and 9.

Subdivided wells may be formed as part of microplates, such as microplate 20 of FIG. 1. Microplates generally comprise sample holders having a frame and a plurality of individual sample wells for holding a corresponding number of samples, or, as described here, a corresponding number of sample subarrays. Microplates may have any suitable overall shape and size, and any suitable number, shape, size, and/or arrangement of wells. In some embodiments, microplates may be rectangular in shape, with cylindrical, hexahedral or frustoconical wells arranged in rectangular arrays, enabling the sample holder to be used with standard microplate equipment, such as handlers, washers, and/or readers, among others.

Microplates may be designed and manufactured as desired, for example, in accordance with industry standards published by the Microplate Standards Development Committee of the Society for Biomolecular Screening. The industry-standard frame has a major dimension X of 127.76 millimeters (mm) ±0.5 mm, a minor dimension Y of 85.48 mm ±0.5 mm, and a height Z of 14.35 mm ±0.76 mm, although other dimensions are possible. In addition, the rigidity of an industry-standard microplate is specified such that at any point along the sidewalls, the differential displacement is no greater than 0.50 mm between an applied load of 0.10 kilograms (kg) and an applied load of 1.00 kg. The frame may include a base configured to facilitate handling and/or stacking, and a notch configured to facilitate receiving a cover. The following table shows three preferred industry-standard well configurations, where $D_C$ is the distance from the left edge of the plate to the center of first well column, and $D_R$ is the distance from the top edge of the plate to the center of the first well row:

| Number of Wells | Arrangement of Wells | $D_C$ (mm) | $D_R$ (mm) | Pitch (mm) Between Wells | Density (/mm$^2$) of Wells |
|---|---|---|---|---|---|
| 96 | 8 × 12 | 14.38 | 11.24 | 9 | 1/81 |
| 384 | 16 × 24 | 12.13 | 8.99 | 4.5 | 4/81 |
| 1536 | 32 × 48 | 11.005 | 7.865 | 2.25 | 16/81 |

The color and material of the microplate may be selected to facilitate particular applications, for example, as shown in the following table:

| Application | Preferred Plate Color and/or Material |
|---|---|
| DNA Libraries/Cell Culture | Clear Polystyrene |
| Fluorescence | Black Polystyrene |
| Luminescence | White Polystyrene |
| High Temperature/Solvent Resistant | Clear Polypropylene |
| Adherent Cell Assays | Clear Bottom (Black or White) |
| DNA Quantization | Clear UV Transparent |

In preferred embodiments, the microplate may be configured for optical detection of assay results from below the microplate, that is, configured to detect light received below the microplate from the bottom of the microplate wells. Accordingly, the bottom may be substantially transparent to visible, UV, and/or IR light. Furthermore, the bottom may be thin enough to achieve optical resolution of results from individual sub-wells and/or individual cells disposed within the sub-wells. Exemplary thicknesses include less than or equal to about 2 mm, 1 mm, 0.5 mm, and/or 0.25 mm, among others, including 0.9 mm and 0.17 mm, among others. Further aspects of optical detection from below the microplate or other sample holder are described below in Section III.

B. Subarray Inserts

Samples may be arrayed in subarray inserts that include a plurality of spatially arrayed sub-wells, as described above. The inserts, also termed subarray holders or buttons, may be disposed removably in microplates with wells that are subdivided using the subarray inserts. Alternatively, the subarray inserts may be designed to include outer walls, so that each insert defines both a well and sub-wells. In these cases, the inserts may be disposed removably in any suitable frame.

Subarray inserts generally comprise any separate structure or device capable of determining the relative positions of a subarray of samples within a frame, microplate well, or other suitable holder or container. The inserts may be small enough to be contained by and viewed in a well of a standard 96-well microplate, as described above, and thus may be less than about 81 mm$^2$. Subarray inserts may be partitioned to form compartments for holding samples, for example, by defining subarrays of apertures or sub-wells, as described above in part A of this section. Alternatively, subarray inserts may be nonpartitioned, generally including a common planar surface for binding samples and/or analytical materials. Examples of nonpartitioned subarray inserts include sheets, chips, and wafers, among others.

Subarray inserts generally comprise subarrays of apertures or sub-wells formed in a generally planar holder. The apertures are through-holes or channels that extend between opposing surfaces of the insert, generally between the upper and lower surfaces during use in a microplate or other frame. Alternatively, the inserts may include sub-wells that extend incompletely from the upper surface toward the lower surface, and thus are not in fluid communication with the lower surface. The apertures or sub-wells may be arrayed, shaped, sized, and spaced to maximize sample capacity and minimize sample cross-contamination, as appropriate, and generally as described above for sub-wells formed integrally in microplates. In addition, the cross-sectional shape of sub-wells or apertures may include involutions to provide increased surface area, for example, a rosette cross section, as described below in Example 4.

Aperture dimensions generally are determined by dimensions of the subarray insert. Aperture lengths generally are at least substantially equal to the thickness of the subarray inserts; preferred holders have a thickness in the range of about 0.1 mm to 2 mm, or about 0.2 mm to 1.5 mm. Aperture diameters (or widths) may be about 20 microns to about 500 microns, or about 50 microns to about 300 microns. The resulting volume or sample capacity of an aperture may be about 5 nL to about 500 nL, or about 20 nL to about 100 nL. Minimum side-to-side spacing between apertures may be at least about 25%, 50%, or 100% of the aperture diameter, among others. For example, closest perimeters of adjacent apertures, each having a diameter of 100 microns, may be about 25 microns, 50 microns, or 100 microns, among others.

Subarray inserts (or microplate sub-wells) also may include features that facilitate retention of sample and/or reagents, promote contact (and thus mixing) between liquid contents of aligned apertures, and/or reduce cross-contamination between sub-wells or apertures. Sub-wells or apertures in a subarray insert may have walls (inner and/or outer) with a distinct composition and/or surface property relative to the upper and/or lower surfaces of the subarray insert. For example, upper and/or lower surfaces of a subarray insert may be hydrophobic, and the aperture/sub-well or well walls may be hydrophilic, or vice versa. In addition, walls of apertures or sub-wells may include binding moieties or may be coated with materials that preferentially bind samples and/or reagents, for example, antibodies. Furthermore, upper and/or lower surfaces of a subarray insert may include a reflective material, generally as a coating. The coating may amplify a signal before measurement. Moreover, upper and/or lower surfaces of a subarray insert may include a cover that extends over end portions of some or all of the apertures/sub-wells in the subarray insert. The cover may be attached to the subarray insert before or after loading each aperture/sub-well with sample and/or reagents. The cover may be a semi-permeable membrane, such as a porous polymer or microfiber material. The semi-permeable membrane may prevent passage of materials based on size, for example, preventing the loss of cells from an aperture/sub-well, and also may facilitate retaining liquid in the aperture/sub-well.

Optical properties of a subarray insert may vary based on aperture/sub-well proximity. For example, each aperture/sub-well may be surrounded by a transmissive ring or sleeve of generally transparent material. In turn, the sleeve may be surrounded by an optical cladding of generally opaque material. The optical cladding also may have a lower index of refraction than the sleeve to promote total internal reflection at the interface between the sleeve and the cladding. This arrangement may limit optical cross-talk between adjacent apertures or sub-wells and may promote transmission of light from the end of the sleeve.

A subarray insert may have additional features to assist in identifying samples and/or analytical materials (reagents) arrayed in the insert. For example, the insert may have an orienting feature that defines aperture/sub-well positions within an array. The orienting feature may be any asymmetric aspect of the insert, such as a mark, label, aperture/sub-well arrangement, or overall shape. The subarray inserts may be configured to include orienting structure that defines the orientation in which the inserts are received by a frame (see below). For example, the subarray inserts may be configured to include a notch(es) or ridge(s) that is received by a generally complementary structure at a receiving site of a frame, and/or may have an asymmetric shape so that the inserts can be received in only one orientation by a frame. Alternatively, or in addition, the inserts may include a detectable code, such as symbols, shapes, patterns, stripes, and/or so on, which may be optically detectable. The detectable code may distinguish the subarray inserts and their subarrays in a mixture of such inserts, for example, in a randomly distributed set of subarrays.

In some embodiments, the subarray inserts may be fashioned as wells. Such inserts may provide the function of the outer wall and bottom of a microplate well. Accordingly, any suitable frame may be used to form an array in which such inserts are positionally disposed. The frame generally includes any structure capable of defining position and/or orientation of the subarray inserts within an array. The frame may include a plurality of predefined receiving sites for receiving the subarray inserts. The receiving sites may be openings, depressions, prongs, bumps, or any others suitable mating structure that may define the position and/or orientation of the subarray inserts. The frame may lack fluid-retaining bottom and/or side walls, because the frame may not be required to contact fluid. Accordingly, the frame may be reusable without concerns about cross-contamination between sequential experiments. Exemplary frames include standard microplates. Other exemplary frames include microplates formed without well bottoms and/or with side walls that are shortened or have openings, thereby enabling removal of the subarray inserts after use.

Further aspects of subarray inserts are described below, in Examples 4-6, and in the following U.S. provisional patent applications, which are incorporated herein by reference: Ser. No. 60/348,027, filed Oct. 26, 2001; and Ser. No. 60/421,280, filed Oct. 25, 2002. Exemplary codes are described in the patent applications listed above under Cross-References, which are incorporated herein by reference.

C. Manufacture of Microplates and Subarray Inserts

Microplates with subdivided wells may be formed by any suitable methods using any suitable materials. In some embodiments, the frames, wells, and/or sub-wells are formed unitarily. For example, microplates may be molded, stamped, machined, etched, and/or the like, using a suitable material, such as polystyrene or polypropylene, to form both the wells and their sub-wells. Alternatively, standard microplates may be converted into superpositional arrays of wells and sub-wells either by the further addition of inner walls within the standard microplate (see below), or by the removal of portions of walls from within the standard microplate. One possible embodiment of such a converted standard microplate is described in more detail in Example 2 below.

Alternatively, wells and sub-wells may be formed of separate components. For example, some or all of the sub-wells in a well may be included in a separate insert that is introduced into the well after the well is manufactured (generally as part of a microplate). The insert may define the inner walls and the sub-wells completely or in concert with the well. Once introduced, the insert may be movable (e.g., held in place by gravity and/or friction) or fixed in position (e.g., using an adhesive, welding, a portion of the well (such as tabs), and/or the like).

A subarray insert may be formed of glass (such as sol-gels and ceramics, among others), an elastomer, composites, laminates, plastic, film, metal, matrices of biological materials, and/or combinations of these and/or other materials, including solids and/or gels. The insert may be shaped and/or dimensioned to match the shape of the well, for example, a circular insert for a circular well or a square insert for a square well. Alternatively, the insert may be shaped and/or dimensioned to be mismatched to the shape of the well, for example, a square insert for a circular well, or vice versa. The insert may include a code or marking to identify the insert and/or samples carried by the insert, and/or to orient the insert. In some cases, the shape and/or size of the insert, relative to the shape and/or size of the well, may help to orient the insert within the well.

In some embodiments, subarray inserts are formed at least substantially of glass. For example, the insert may be a generally planar sheet of glass that has been etched and/or ablated to define the apertures/sub-wells. Alternatively, glass aperture arrays may be formed by bundling individual aperture tubes and drawing the bundle to the desired size. In addition, glass aperture arrays may be formed as an assembly of glass fibers, with each glass fiber surrounded by a cladding material, where exposure to acid or some other suitable etching material removes the glass fiber and leaves an aperture in its place. Glass aperture arrays formed by some of these methods are available from Collimated Holes, Inc., of Campbell, Calif.

Exemplary methods of forming subarray inserts are described in more detail below, particularly in Example 5-6, and in the following U.S. provisional patent applications, which are incorporated herein by reference: Ser. No. 60/348,027, filed Oct. 26, 2001, and Ser. No. 60/421,280, filed Oct. 25, 2002.

II. ASSAY METHODS

This section describes assay methods that may be suitable for analyzing samples in microplates having subdivided wells, formed either integrally or as subarray inserts; see FIGS. 3 and 4.

A. Arraying Samples and/or Reagents using Subdivided Microplates

Samples may be arrayed in (or on) subdivided microplates for exposure to analytical materials (reagents). Samples generally comprise any suitable target, such as a biological entity (cells, viruses, phages, among others), enzymes, receptors, ligands, antibodies, nucleic acids, proteins, and/or so on, although nonbiological materials may constitute the target in some embodiments. Reagents generally include any material or treatment (cell, mixture, complex, compound, and chemical or physical modulator, among others) that may interact with a sample. Interaction includes any measurable effect, such as binding, a phenotypic change, or a physical change. Examples of reagents for cells (termed cell-analysis materials) include modulators, such as drugs; ligands/receptors, such as antibodies, hormones, and cell-surface receptors; transfection materials; cell selectors, such as cell-specific or cell-restricted antibodies; local capturing agents; biological entities, such as cells, viruses, phages, and the like; and assay reagents, such as labels (dyes), among others.

Samples and reagents are contacted, combined, or exposed to each other to measure interactions and/or to perform assays. Samples may be disposed in microplate sub-wells or subarray inserts first and then reagents introduced subsequently. Alternatively, reagents may be introduced first and then samples introduced subsequently. When introduced into a sub-well or aperture, samples and/or reagents may attach to the sub-well or aperture floor/walls, and/or may be generally diffusible within the sub-well or aperture.

Samples and/or reagents may be introduced by gravity, pressure, capillary action, and/or diffusion among others. Any suitable fluid transfer system may be used, including a needle, a set of needles, a multi-channel pipeting device, or a modified inkjet printhead, among others.

Further aspects of samples and reagents that may be used in array/subarray assays are described in more detail in the patent applications identified above under Cross-References, which are incorporated herein by reference, particularly U.S. patent application Ser. No. 09/549,970, filed Apr. 14, 2000; U.S. patent application Ser. No. 09/694,077, filed Oct. 19, 2000; and U.S. patent application Ser. No. 10/120,900, filed Apr. 10, 2002.

B. Assays with Adjustable Fluid Communication

Wells carrying sub-wells, as described herein, may be used in novel ways in various assay procedures. Generally, apparatus with such wells may be used to perform any assay or other procedure requiring or benefiting from the exposure of a plurality of biological or chemical samples to fluid reagents under identical physical conditions. Such procedures may include, for example, cell phenotyping, microscale chemical syntheses, and high-throughput chemical or drug compounds, among others. Such procedures may include preparing the individual samples, and then independently disposing the samples in the sub-wells of the apparatus to form a subarray. Individual samples of the subarray may be identified based on their positions within the subarray. Alternatively, or in addition, the samples may be prepared in situ, that is, in the sub-wells, for example, by chemical synthesis, transfection, or the like. In either case, the samples positioned at sub-wells of a well may be treated as a group by adding reagent fluid to a level within the well greater than the height of the inner walls of the well, so that the reagent is in fluid communication with the desired plurality of samples. This method ensures that each sample interacts with a fluid reagent of identical concentration, pressure, temperature and the like, aside from unavoidable fluctuations in these physical properties within the reagent fluid.

Figure 3A:
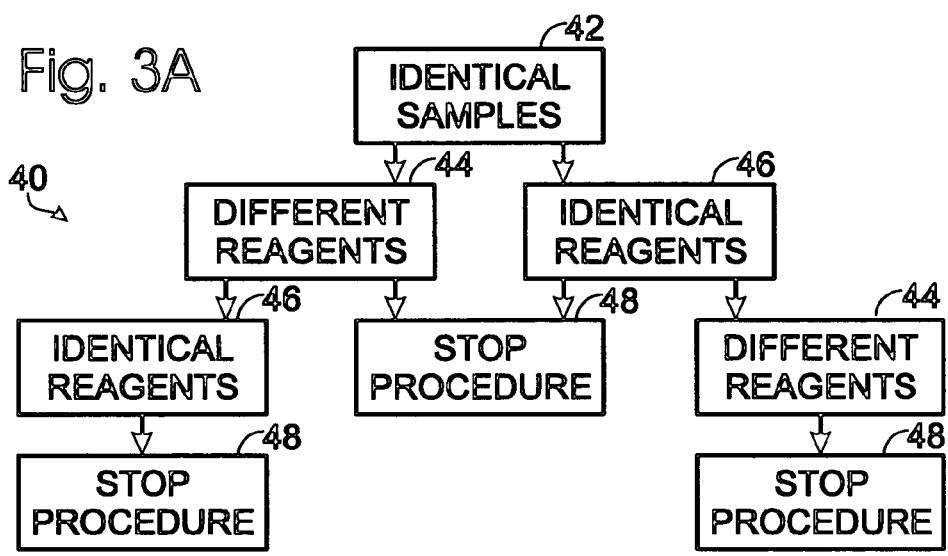
FIG. 3 is a pair of flowcharts showing embodiments of assay methods that may be conducted with the sample holder of FIG. 1, in accordance with aspects of the present teachings.

FIG. 3A shows a method 40 in which subdivided wells, as described herein, may be used to perform procedures requiring or benefiting from the exposure of identically prepared samples 42 to various reagents. The samples may be prepared in a fluid medium and inserted into the sub-wells of the apparatus by adding the sample fluid to one or more sample wells to a level within the well greater than the height of the inner walls of the well, so that the sample fluid has access to all sub-wells of the well. The samples may be allowed to adhere, bind, or otherwise attach themselves to the bottoms and/or inner walls of the sub-wells, and then the sample-bearing fluid medium may be removed. The result is a plurality of sub-wells that have been prepared from a continuous fluid medium so that the samples are likely to be very similar, or effectively identical, in their substantive properties.

FIG. 3A shows exemplary addition sequences for exposure of the sample array to reagents. Different reagents 44 and/or identical reagents 46 may be added to the various sub-wells in any suitable sequence and any suitable number of times until the procedure is stopped, shown at 48. Exposure of the sample array to different reagents 44 or identical reagents 46 is determined by the level to which the reagent(s) is added. Different reagents 44 are added to levels less than or equal to the height of the inner walls of the sample well, such that each reagent fluid is only in fluid communication with the sample of only one of the identically prepared sub-wells. In some embodiments, due to surface tension, sub-wells may be addressed individually with fluid added to a level that is slightly greater, locally at the sub-well, than the height of the inner walls. In all cases, sub-wells are addressed individually by adding a volume of fluid to each sub-well that is small enough to maintain fluid isolation of the sub-wells. Alternatively, or in addition, identical reagents, shown at 46, may be added before or after addition of the different reagents by adjusting the volume to a level above the sub-well level so that all sub-wells are in fluid communication.

Figure 3B:
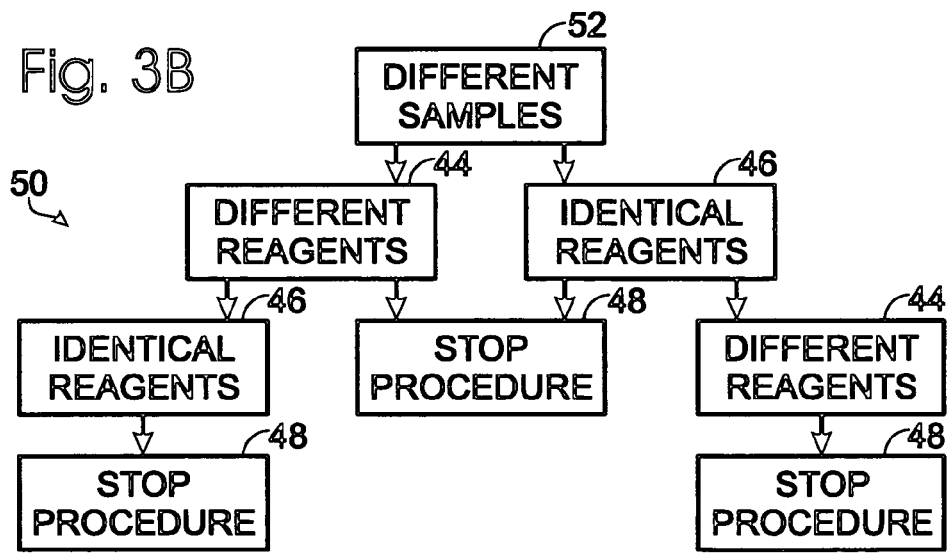

FIG. 3B shows a method 50 in which subdivided wells, as described herein, may be used to perform procedures requiring or benefiting from the exposure of different samples 52 to various reagents in a single or a multi-step process. Different samples 52 may be prepared separately and inserted into the sub-wells of the apparatus by adding the sample fluid to one or more sub-wells to a level less than the height of the inner walls of the well, to prevent fluid communication between sub-wells. The samples may be allowed to adhere, bind, or otherwise attach themselves to the bottoms and/or inner walls of the sub-wells, and then the sample-bearing fluid medium may be removed. The result is an array of different samples. Different reagents 44 and/or identical reagents 46 may be added to the various sub-wells indefinitely as is appropriate to the procedure.

The various methods described above are not the only possibilities, and are not intended to limit or define the entire scope of the present teachings. These methods may be generalized to include any procedure where reagents are added to differently or identically prepared samples in one or more steps, where the method utilizes the sub-well structure of the apparatus to facilitate either the preparation of identical (or different) samples or the exposure of samples to an identical (or different) reagent(s).

FIG. 4 shows exemplary methods for analyzing cells in positional arrays that are formed in sub-wells. The sub-wells are addressable individually or as a group based on the fluid volume/level added, as described above.

FIG. 4A shows a method 60 using sub-wells to form and analyze a positional array of different cell types. The sub-wells are each addressed individually, as shown at 62, with a different type of adherent cell 64, without overfilling sub-wells 66 (and mixing the different cell types). The cells are allowed to adhere to the sub-wells, as shown at 68, thereby transforming the sample well into a positional array 70 of different cell types 64. In some embodiments, the sub-wells may be placed in fluid communication after cell types 64 have attached, but before a test reagent is introduced, thereby reducing problems associated with evaporation of cell media as the cells are incubated. Alternatively, or in addition, cell types that grow in suspension may be introduced into the sub-wells, if the suspension cell types are attached to the sub-wells, or structures therein, for example, via specific (e.g., biotin-avidin) and/or nonspecific interactions. Next, different reagents may be added separately to the individual sub-wells, using a volume that does not exceed the capacity of each sub-well, so that each cell type experiences a different reaction condition. Alternatively, or in addition, reagent 72 may be added to overfill all of the sub-wells, as shown, so that each cell type experiences the same reaction condition.

FIG. 4B shows a method 80 using sub-wells to modify and analyze a single cell line by transfection with different transfection reagents. Sub-wells 66 each are filled with cells 82 of the same type, as shown at 84. Next, the cells are allowed to adhere and/or bind to surfaces of the sub-wells, as shown at 86, to form a positional cellular array 88 of substantially identical members. For example, a suspension of the cells in media may be added in a volume that addresses all the sub-wells together. Next, the media are removed, and a different transfection may be performed in each sub-well, as shown at 90, by individually addressing each sub-well with a different transfection reagent 92. By individually transfecting each sub-well, a positional array 94 of transfected cells is formed within a single sample well 96. Positional array 94 may be treated together with a reagent 72, by overfilling the sub-wells, as shown at 98, or the transfected cell populations 100 within the array may be treated individually by partially filling the sub-wells. Transfection of cells in sub-wells may be especially powerful in assays that reduce gene expression for target validation and/or functional genomics, for example, assays that use antisense nucleic acids, RNAi, etc.

An array of subarrays may be used to perform experiments in which cell populations are exposed to different reagents. The reagents may be candidate cell modulators, for example, drug candidates, chemical compounds, ligands, viruses, transfection materials (such as nucleic acids), extracts, lysates, and/or the like. In some embodiments, cell populations may be disposed so that each subarray includes the same set of cell populations, attached at the same relative or absolute position within the subarray. Accordingly, the cell populations may be identified by their positions within the subarray. By contrast, each subarray may be contacted with a different reagent in each well in an array, so that the well position identifies the reagent added to that particular well. This approach may allow candidate cell modulators each to be tested for the potency and selectivity of their effect on a plurality of different cell populations.

Further examples of arrays, including positional and nonpositional arrays, exemplary transfection materials and transfection assays, and other assays that may be conducted with arrays, particularly cell arrays, are described in more detail in the patent applications identified above under Cross-References, which are incorporated herein by reference, particularly U.S. patent application Ser. No. 09/549,970, filed Apr. 14, 2000; U.S. patent application Ser. No. 09/694,077, filed Oct. 19, 2000; and U.S. patent application Ser. No.10/120,900, filed Apr. 10, 2002.

III. DETECTION SYSTEMS

Sample signal (or characteristics) from an array may be measured before, during, and/or after an assay procedure. Sample signal may be an averaged signal from all samples over the entire subarray, for example, to identify the presence of a rare positive sample among many subarrays in a library screen. Alternatively, sample signal may be individual signals from each sub-well in the subarray or plural signals from within a sub-well, such as signals from individual cells or subcellular structures. Before, during, or after measuring sample signal, the subarray, and thus samples, reagents, and/or assay conditions for the array, also may be identified by determining the position of the subarray within a higher order array, such as identification of well position with a microplate. Alternatively, or in addition, a code carried by the subarray may be read to identify the subarray. The steps of measuring sample signal and identifying the subarray generally may be performed in any order, and each step may be performed selectively on specific subarrays. For example, in some cases, the subarray may be identified only for subarray inserts that exhibit a specific sample characteristic, such as showing a positive signal. Alternatively sample signal may be measured only for subarrays that have a specific code(s) or position among subarrays in a microplate. Moreover, these steps may be performed using any suitable detection device, such as a microscope, a film scanner, a fiber optic bundle, or a plate reader, among others.

Sample signals or characteristics, array codes, and other measured quantities may be determined using any suitable measurement method. The measured quantities generally comprise any measurable, countable, and/or comparable property or aspect of interest. The detection methods may include spectroscopic, hydrodynamic, and imaging methods, among others, especially those adaptable to high-throughput analysis of multiple samples. The detection methods also may include visual analysis. Measured quantities may be reported quantitatively and/or qualitatively, as appropriate. Measured quantities may include presence or absence, or relative and/or absolute amounts, among others.

Figure 5:
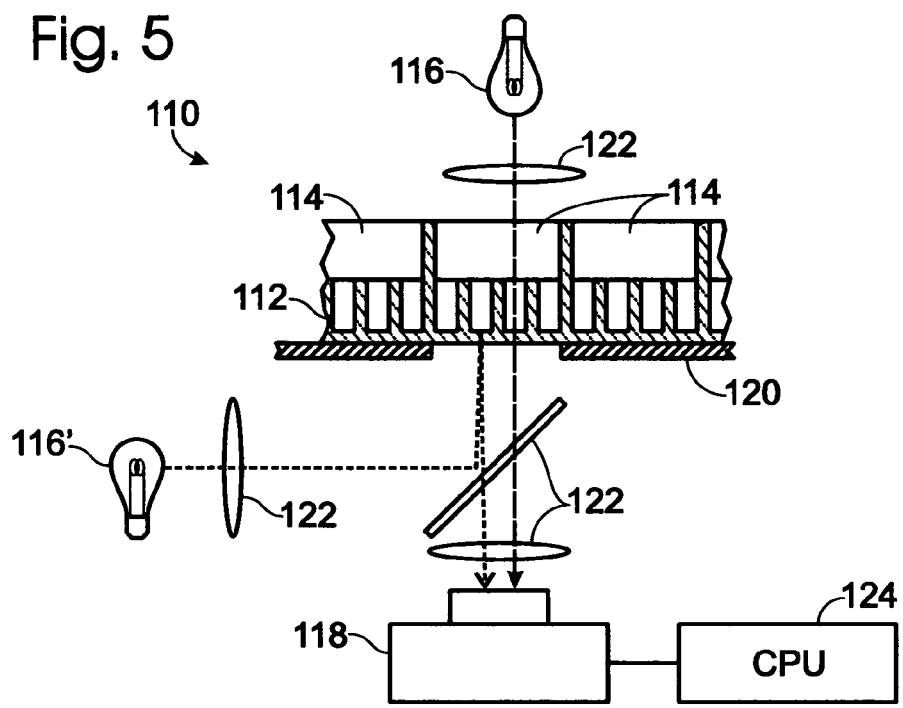
FIG. 5 is a schematic side view of a detection system for detecting assay results from arrays of cells formed in subdivided wells of a microplate, in accordance with aspects of the present teachings.

FIG. 5 shows an exemplary system 110 for optically detecting assay results from a microplate 112 with subdivided sample wells 114. System 110 generally includes a light source, 116 or 116', to illuminate samples in microplate 112, and a detector 118 to receive and measure optical signals produced by sample illumination. The system also may include a stage 120 to support the microplate, optics 122 disposed between source 116, 116' and detector 118, and/or a digital processor 124.

Light source 116, 116' generally comprises any device for producing light of any suitable spectrum, intensity, and/or coherence, among others. Suitable light sources may include arc-lamps, light-emitting diodes, and lasers. Light source 116 may be disposed on an opposite side of microplate 112 as detector 118, in this case above microplate 112, to provide trans-illumination. Trans-illumination may be used, for example, to measure absorbance, scattering, photoluminescence, or microscopic pattern (bright field, dark field, DIC, Nomarski, phase contrast, etc.). Alternatively, light source 116' may be disposed on the same side of microplate 112 as detector 118, in this case below the microplate, to provide epi-illumination. Epi-illumination may be used, for example, to measure photoluminescence, such as fluorescence or phosphorescence, among others. Alternatively, light source 116 or 116' may be disposed at any other suitable angle(s) or position relative to detector 118 and microplate 112 to perform, for example, measurements of total internal reflection. In some embodiments, such as measurements of sample bio-, chemi-, or electroluminescence, a light source may not be required.

Detector 118 generally comprises any device for measuring light. Detector 118 may be a point detector, that is, a detector configured to measure a single value at a time, such as a photomultiplier tube or a photodiode. Alternatively, or in addition, detector 118 may be an image detector, configured to measure plural signals that are spatially distributed, generally using a detector array. Exemplary image detectors include CCD, CMOS, or photodiode arrays, among others.

Detector 118 may be configured to detect a whole microplate, part of a microplate, a well, a sub-well, or any portion thereof, to provide a single value or spatially distributed values, such as values from each sub-well in a well or set of wells. The detector may read from more than one well or sub-well, simultaneously and/or sequentially. For example, the detector may detect (typically image) light from two or more wells (or sub-wells) at the same time, distinguishing wells (or sub-wells) by their relative positions. Alternatively, or in addition, the detector may detect light by moving from (sub-)well(s) to (sub-)well(s), through movement of the detector, the sample holder, or both. Accordingly, detector 118 may be fixed or may be configured to move relative to microplate 112, to enable scanning. When detector 118 is fixed, stage 120 may be configured to move portions of microplate 112 past detector 118. In some embodiments, an optical element (see below) may be movable to direct light from different portions of the microplate to the detector.

Detector 118 may have any suitable position relative to microplate 112. Accordingly, the detector may be separated from the microplate by optics 122. Alternatively, the detector may be positioned close to the microplate without intervening optics or may be in contact with the microplate. The detector may be disposed above the microplate, or, as shown here, the detector may be disposed below the microplate to read signal from the bottom of the microplate.

In some embodiments, detector 118 includes a compensation mechanism that measures and compensates for fluctuations in the intensity of source 116 or 116' to correct the detected signal based on these fluctuations.

In yet other embodiments, array holders may be physically coupled to imaging devices, to enhance the imaging capability of the assay system, increasing reliability and throughput. For example, glass-imaging fibers may be constructed to contain small recesses at one end, so that the recesses are an extension of the optical detection fibers.

Optics 122 generally comprises any optical elements for modifying, focusing, and/or collecting light. Exemplary optical elements include lenses, filters, gratings, mirrors, apertures, optical fibers, and/or the like. Optics 122 may alter light intensity, wavelength, polarization, spatial distribution, coherence, direction, and/or the like. The optics may be disposed at any suitable position(s) within system 110, including between the light source and the microplate/sample and/or between the microplate/sample and detector. For example, an array of photodetectors and the sample wells may be separated by an intervening array of optical fibers, which direct light to the detector(s) from the sample wells (or sub-wells).

Processor 124 generally comprises any digital processing system that interfaces electrically with electronic or electrical components of system 110. Accordingly, processor 124 may be configured to send signals to and receive signals from the components and thus control operation of the components or store data received therefrom. Suitable components for electrical interfacing may include light source 116 or 116', detector 118, stage 120, optics 122, and/or a user interface (for example, a keyboard or keypad, a monitor, and/or a printer). Accordingly, processor 124 may receive, store, and process data from detector 118. Alternatively, or in addition, processor 124 may activate, move/position, and/or coordinate operation of a light source, a detector, a stage, and/or optics, among others.

IV. EXAMPLES

The following examples describe selected aspects and embodiments of the present teachings, including methods and apparatus for forming and analyzing sample subarrays in individual wells of a microplate. These examples are included for illustration and are not intended to limit or define the entire scope of the present teachings.

Example 1

Microplates with Subdivided Wells

This example describes embodiments of microplates having integral sub-wells; see FIG. 6.

Figure 6A:
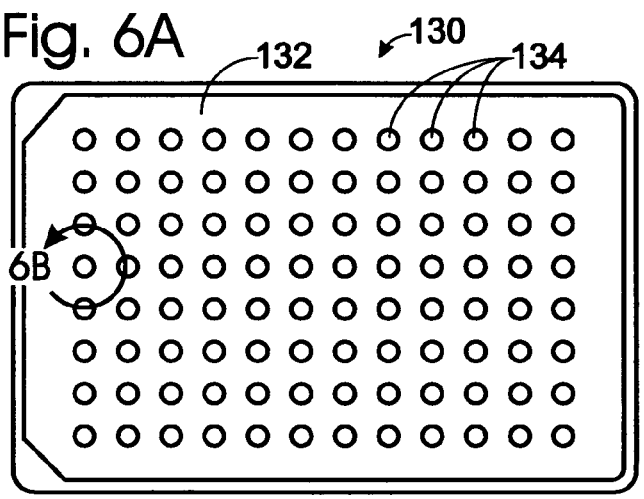
FIG. 6A is a top plan view of a microplate formed with subdivided wells, in accordance with aspects of the present teachings.

FIG. 6A shows microplate 130 having a frame 132 and a plurality of wells 134 disposed in the frame. Here, microplate 130 is configured to have 96-wells in eight rows of twelve columns. However, the size, shape, number, and disposition of wells 134 may be selected based on the application, as described above in Section I.

Figure 6B:
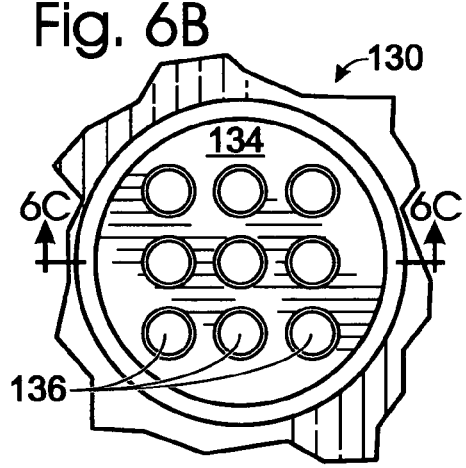
FIG. 6B is an enlarged fragmentary view of one of the subdivided wells of the microplate of FIG. 6A.
Figure 6C:
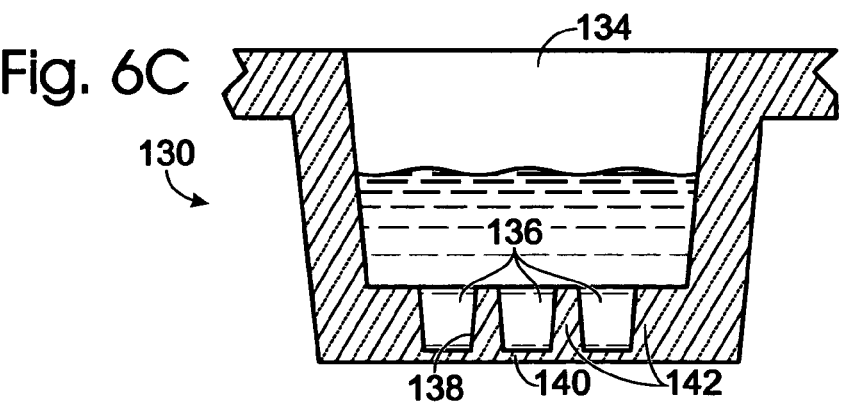
FIG. 6C is a sectional view of the subdivided well of FIG. 6B taken generally along line 6C-6C of FIG. 6B.

FIGS. 6B and 6C show magnified and sectional views, respectively, of one of wells 134 with sub-wells 136 visible. Here, each well 134 includes nine sub-wells that are frustoconical. However, sub-wells 136 may have any suitable size, shape, number, and disposition within each well, as described above in Section I. FIG. 6C shows sub-wells 136 formed as recesses 138 in the material of microplate 130. As shown, bottom portion 140 defined below each sub-well may be thinner than the average thickness of microplate 130 and/or thinner than adjacent portions 142 of well 134, which may form the walls that separate the sub-wells. A thinned bottom portion below each sub-well may facilitate improved optical access to the sample in sub-well 136 for detection from below microplate 130, as described above in Section III. Alternatively, the bottom portion of the sub-well may have a thickness that is substantially the same as, or greater than, adjacent portions 142 of well 134 or the average thickness of microplate 130.

Example 2

Conversion of a Standard Microplate

This example describes how a standard microplate may be converted into a microplate with subdivided wells. A standard microplate typically has wells with uniform depth, but may be converted into a superpositional array of wells and sub-wells, where the wells have different relative depths, in accordance with aspects of the present teachings.

Standard microplates may be configured as superpositional arrays of wells and sub-wells by reducing the height of one or more inner walls of the microplate. For example, an industry-standard 1536-well microplate may be converted into a superpositional array of 96 wells, each containing 16 sub-wells. To make such a conversion, various inner walls of the standard microplate may be machined to a lower height than the other walls, to create the desired superpositional array. More generally, any desired sub-well structure may be created by altering (e.g., lowering or raising) the height of some of the walls of a standard microplate (e.g., by removing or adding material), or by adding new walls within a standard microplate, or by a combination of these two techniques, among others.

Example 3

Microplates with a Hierarchy of Sub-wells

Figure 7:
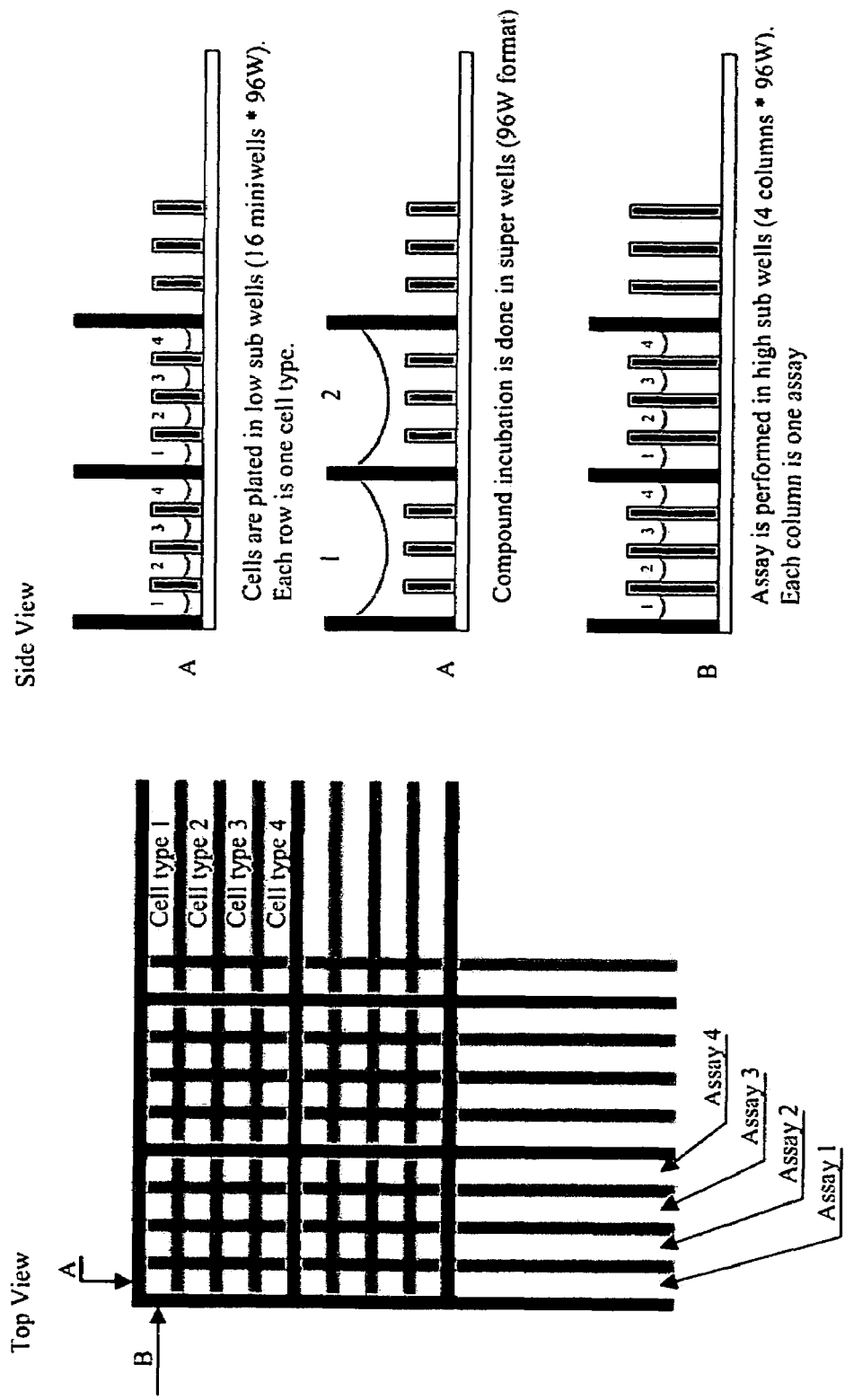
FIG. 7 is a schematic representation of an exemplary microplate, with wells subdivided into a two-level hierarchy, being used to perform a plurality of assays on a plurality of cell types in each well, in accordance with aspects of the present teachings.
Figure 8:
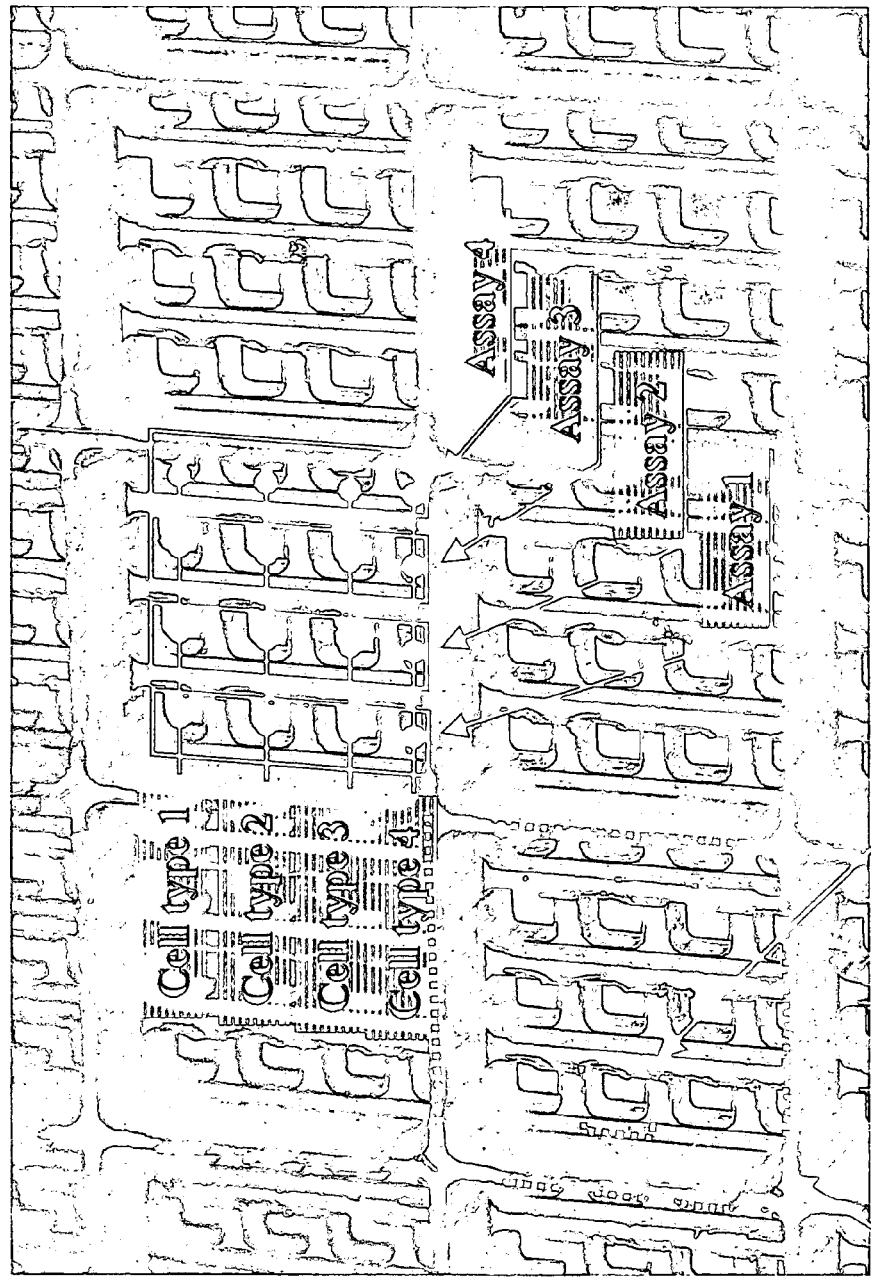
FIG. 8 is a photograph of another exemplary microplate fabricated with the two-level hierarchy of FIG. 7, with exemplary positions of different cell types and assays indicated, in accordance with aspects of the present teachings.

This example describes microplates with a hierarchy of sub-wells and methods of using these microplates for performing biological assays with cells; see FIGS. 7 and 8.

FIG. 7 shows an exemplary microplate with wells subdivided into a hierarchy of fluid compartments to provide three-levels of adjustable fluid communication. The microplate may be used, for example, to perform a plurality of different assays on a plurality of different cell types in each well. Furthermore, each well may be used to test the effect of a substance, such as a candidate modulator, on the different cells type in the different assays. Alternatively, the microplate may be used to contact sets or groups of different cell types within each well with the same reagent. For example, each group of different cell types may be placed in fluid communication with a fluid containing a transfection material, so that each of the cell types is exposed to, and transfected with, the transfection material. Alternatively, or in addition, each group of different cell types may be placed in fluid communication with a different assay reagent, such as a dye to label each group.

The microplate, shown in a top view on the left of FIG. 7, may include a plurality of wells disposed in a frame. The wells may be defined and separated by an outer wall, shown in black. Each well may be divided by at least two inner walls (or sets of inner walls) of different height, with each set (or portions thereof) shorter than the outer wall. A first set of the inner walls, shown in orange, may be of intermediate height. The first set of inner walls may extend between opposing positions of the outer wall, to form a series of troughs or channels within the well. A second set of the inner walls, shown in gray, may be shorter than the first set of inner walls. The second set of inner walls may extend transverse to the first set of inner walls, between opposing positions of the troughs to divide each trough and subdivide each well into sub-wells. The troughs and sub-wells may be arrayed generally orthogonal to one another, for example, so that the sub-wells are disposed in individually addressable rows or columns within each well.

Samples, such as different cell types (indicated as cell types 1-4), may be disposed in sub-wells. The different cell types may be disposed in individual sub-wells, for example, by placing cells of one type in each sub-well, in a volume of fluid small enough to produce fluid isolation from other sub-wells. Each cell type (or each mixture of cell types) may be disposed in a row (or column) within the well. In some examples, each cell type may have a corresponding position in each well of the microplate. For example, in the present illustration, cell type 1 occupies the first row of sub-wells in every well, cell type 2 the second row of sub-wells, and so on.

FIG. 7, top right panel, shows a sectional view of wells of the microplate, taken along line "A" from the top view on the right, after plating different cell types 1-4 in the first column of sub-wells (and first column of troughs). Cells of each cell type are disposed in a corresponding sub-well in a fluid volume (indicated with a red meniscus) that provides fluid isolation from other sub-wells (and between different cell types). Accordingly, each cell type is restricted to its corresponding sub-well until a suitable proportion (or all) of the cells have attached to the surface of the sub-well (or at least settled in the sub-well). After attachment or settling, sub-wells may be placed in fluid communication during subsequent manipulations without substantial loss of cells from each sub-well and/or mixing of different cell types between adjacent sub-wells.

FIG. 7, middle right panel, shows a sectional view, taken as in the top right panel of this figure, after adding fluid to a level that permits fluid communication between all sub-wells (and thus all cells) within each well. A different (test) compound (or candidate modulator) may be included in the fluid of each well so that each test compound accesses all of the sub-wells in each corresponding well.

FIG. 7, bottom right panel, shows a sectional view of wells of the microplate, taken along line "B" from the top view on the right, after adjusting fluid levels to perform different assays within each column/trough of a well. The fluid levels may be adjusted to place each trough (and column of sub-wells in the well) in fluid isolation from one another. However, the sub-wells within each trough may be in fluid communication, so that a fluid in each trough may access the cells in each sub-well. The fluid may include a reagent(s) to facilitate performance of a suitable assay, and each trough/column may include a different reagent(s). The reagent may include, for example, a specific binding partner (such as an antibody, a ligand, a receptor, etc.), a dye, a modulator, a nucleic acid, and/or the like. In some embodiments, compound (modulator) incubation may be performed after different reagents are addressed in isolation to each trough, such as after the cell types in each trough are transfected with a different nucleic acid.

Other exemplary reagents and/or assays are described in more detail in the patent applications listed above under Cross-References, which are incorporated herein by reference, particularly U.S. patent application Ser. No. 09/549,970, filed Apr. 14, 2000; U.S. patent application Ser. No. 09/694,077, filed Oct. 19, 2000; and U.S. patent application Ser. No. 10/120,900, filed Apr. 10, 2002.

FIG. 8 is a photograph of an exemplary microplate fabricated with the multi-level hierarchy of FIG. 7, in accordance with aspects of the present teachings.

Example 4

Subarray Inserts

This example describes embodiments of subarray inserts that may be placed in microplate wells to subdivide the wells; see FIGS. 9-18. These embodiments may include features that decrease background, amplify signal, and/or increase sample/reagent capacity or retention.

FIGS. 9-18 show exemplary subarray inserts. These inserts, also termed buttons, may be designed to subdivide sample wells within a microplate or may be used as subarray holders for other purposes, such as forming nonpositional arrays, as described above. The inserts comprise an array of compartments or holes, formed in a planar holder, where each hole is an aperture or sub-well. The apertures may extend completely between upper and lower surfaces of the holder. Alternatively, the holes may be recesses or wells that extend incompletely from the upper surface toward the lower surface, but that are not in fluid communication with the lower surface. The holes within a subarray insert may be arrayed in a regular pattern of rows and columns, or they may have an irregular pattern that is defined or random. Some or all of the holes in an array may extend in a generally parallel arrangement.

FIG. 9A shows a microplate assembly 250 having a microplate 251 with a plurality of wells 252 carrying subarray inserts 254. FIGS. 9B and 9C shows subarray insert 254 in more detail submerged in fluid within a well. The subarray inserts may have a generally planar structure so that each insert abuts the bottom of each well. Subarray insert 254 defines plural sub-wells 256 forming a subarray of sample assay sites. Sub-wells 256 may be spaced from each other by side walls 258 and from well surface 260 by sub-well floor 262. Accordingly, sub-wells 256 may be addressed independently and as a group by adding fluid to a level that is below and above, respectively, the top of side walls 258.

FIG. 10 shows an alternative subarray insert 270 supported by the bottom of well 252 and submerged in fluid. Subarray insert 270 includes plural through-holes or apertures 272 that extend between opposing surfaces of insert 270. As shown here, subarray insert 270 may cooperate with horizontal surface 260 of wells 252 to define sub-wells using the apertures.

FIG. 11 shows a sectional view of another subarray insert 280 supported by the bottom of wells 252 and submerged in fluid. Subarray insert 280 may include plural apertures 282 as in subarray insert 270 described above. However, each aperture may be surrounded by optically distinct layers or sleeves of material, a light-transmissive inner layer or sleeve 284 and an outer optical cladding 286 that transmits light poorly.

FIG. 12 shows a plan view of insert 280 and indicates how these layers may be arranged, with sleeve 284 surrounding aperture 282 and cells 288, and optical cladding 286 surrounding sleeve 284. Cladding 286 may be formed of any opaque or other relatively nontransmissive material, such as dark glass. Accordingly, the cladding may minimize cross talk between samples during signal detection.

FIG. 13 shows another embodiment of a subarray insert 290, viewed as in FIG. 12. Aperture 292 may be defined by sleeve 294 with an involuted surface structure. For example, sleeve 294 may include a rosette cross-section for increased surface area and thus increased capacity for sample/reagent bound to the aperture wall. In some embodiments, the width of the opening between each rosette cavity "petal" and the central portion of the aperture may be configured to retain cells in the petals of the rosette, while maintaining a fluid connection to the central portion of the aperture.

Figure 14:
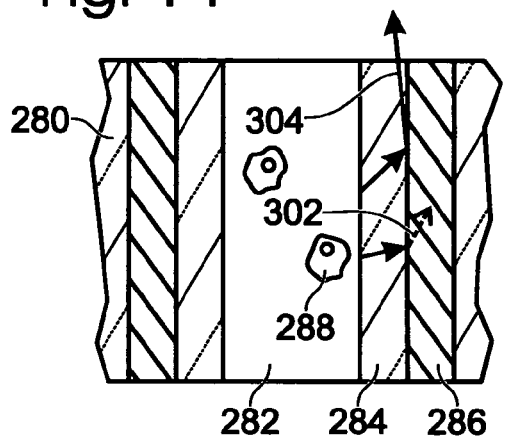
FIG. 14 is a fragmentary sectional view of the subarray insert of FIG. 11, viewed generally along line 14-14 of FIG. 12 and illustrating optical transmission by the sleeve and optical insulation by the cladding, in accordance with aspects of the present teachings.

FIG. 14 is a sectional view of FIG. 12 that illustrates how sleeve 284 and cladding 286 of subarray insert 280 may function to direct optical signals. Light directed through sleeve 284 to cladding 286 at less than the critical angle (measured relative to normal from the interface between the sleeve and the cladding) may be absorbed by the cladding, as shown at 302. However, light directed through sleeve 284 to cladding 286 at greater than the critical angle may be totally reflected internally and thus directed within sleeve 284 toward the exterior surface of the insert, as shown at 304.

Figure 15:
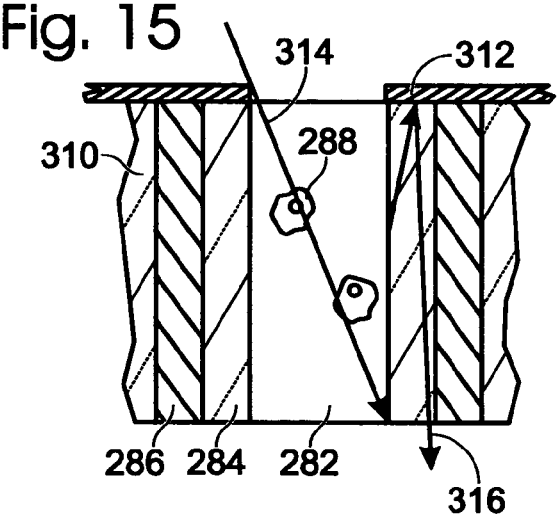
FIG. 15 is a sectional view of an alternative embodiment of the aperture, sleeve, and cladding of FIG. 12, in which a reflective surface is disposed adjacent the sleeve and cladding, in accordance with aspects of the present teachings.

FIG. 15 shows a subarray insert 310 with a reflective layer 312. Layer 312 may amplify signal from an aperture, because layer 312 can reflect light back to a detector. For example, layer 312 may be formed by coating an exterior surface with a reflective material, such as a metal. In use, cells 288 may be excited with light 314 directed at subarray insert 310 at greater than the critical angle (measured relative to normal from the aperture/sleeve interface), so that the light does not enter sleeve 284, but instead produces fluorescence emission from cells 288. Direct signals and reflected signals 316 may be measured together from sleeve 284.

Figure 16:
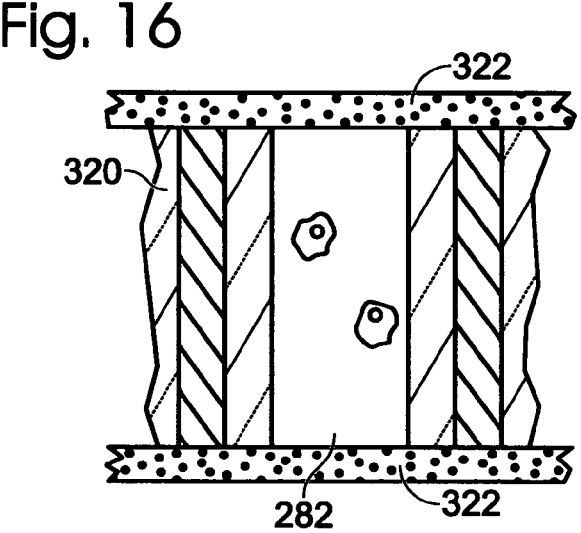
FIG. 16 is a sectional view of another embodiment of the aperture, sleeve, and cladding of FIG. 14, with a cover disposed at each end of the aperture, in accordance with aspects of the present teachings.

FIG. 16 shows a subarray insert 320 with covers 322 over apertures 282. The cover(s) may be disposed over one or both ends of the apertures on an exterior surface(s) of subarray insert 320 and may be membranes formed of a semi-permeable or impermeable material. Cover 322 may facilitate retention inside apertures and may be disposed on insert 320 before or after addition of samples or reagents.

Figure 17:
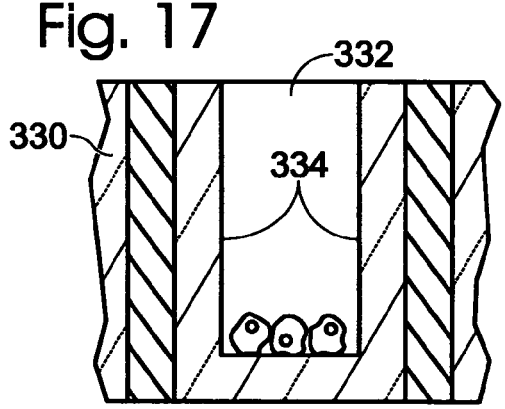
FIG. 17 is a sectional view of yet another embodiment of the aperture, sleeve, and cladding of FIG. 14, in which the aperture is replaced by a sub-well, in accordance with aspects of the present teachings.

FIG. 17 shows a subarray insert 330 defining plural recesses or sub-wells 332 rather than apertures. Cells may attach to side walls 334 and/or to a bottom surface 336 of sub-wells 332. The sub-wells may be formed, for example, by controlled etching to a given depth or by ablation or molding, among others.

Figure 18:
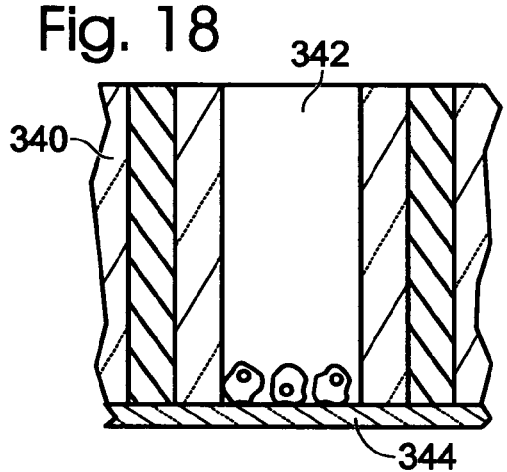
FIG. 18 is a sectional view of still another embodiment of the aperture, sleeve, and cladding of FIG. 14, in which a sheet of material has been attached to a surface of the subarray insert to seal an end of the aperture, in accordance with aspects of the present teachings.

FIG. 18 shows another subarray insert 340 defining plural recesses or sub-wells 342 rather than apertures. Here, sheet 344 is attached to an exterior surface of subarray insert 280 (see FIG. 11), so that apertures 282 are sealed at one end to form sub-wells 342. Sheet 344 may be formed of any suitable material, such as glass or plastic, among others, and may be attached by heat, pressure, an adhesive, light, and/or other suitable mechanism

Example 5

Exemplary Embodiments of Subarray Inserts I

This example describes subarray inserts that define plural apertures.

An exemplary subarray insert may include one-hundred apertures in a rectangular array, for example, formed of ten rows and ten columns of apertures. The apertures may be formed in a glass matrix as through-holes that extend between opposing faces of the matrix. Exemplary dimensions are four millimeters in length and width, with aperture centers disposed every 400 microns along orthogonal axes. Each aperture may have a diameter of 200 microns, so that the minimum distance between adjacent aperture walls is about 200 microns.

In other embodiments, the apertures generally may have any suitable arrangement and any suitable dimensions. For example, the pattern of holes may be hexagonal, which generally fits more holes in the same area while being easier to manufacture. The corresponding holders/inserts are easy to manufacture, and may be scaled up or down as needed.

The position of each aperture within a subarray insert, and thus of sample and/or reagent loaded into each aperture, may be unambiguously defined by one or more orientation marks asymmetrically positioned within the insert. These marks may comprise any structure suitable for identifying orientation, such as a "dead" (i.e., nonetched or unformed) hole in the array.

In cell assays, each aperture may hold a distinct cell type or cell population. Each cell type or population may be individually loaded into each aperture as a pure population, or cell selectors (generally, antibodies) may be bound to the aperture walls first, to select specific cells out of a mixed population passed through each aperture. Cells may be bound and then directly analyzed, or cells may be grown on the aperture walls before analysis. In some embodiments, all apertures may be exposed to a common reagent after loading cells into the array.

Example 6

Exemplary Embodiments of Subarray Inserts II

A subarray insert may be designed to fit into a standard square or circular 96-well microplate, for example, dividing each well into a plurality of one mm-deep sub-wells. The insert may include a 100-micron thick, optically transparent bottom surface, which may be used for detection through the bottom of the sub-wells.

Subarray inserts may be formed using glass fibers to form a fiber assembly. In some embodiments, the fiber assembly may be drawn only (but not fused), leaving interstitial voids between apertures. In an exemplary embodiment, the fiber assembly may include 600-micron apertures created by etching away place-holder glass fibers used to create the initial fiber assembly. Each aperture may include an internal sleeve, which is made from optical glass with a refractive index of 1.56. The sleeve may be impervious to the acid used in the etching process, and the thickness of the sleeve wall may be changed to alter the ratio of open to solid area.

Each aperture also may include a black ring or optical cladding around the sleeve, which may be constructed from Extra-Mural Absorber (EMA). The optical cladding may provide optical isolation for each aperture and sleeve, and reduces or prevents optical cross-talk between apertures. The refractive index of glass used to form the optical cladding may be lower than the refractive index of the sleeve, to provide an interface condition between the cladding and sleeve for total internal reflection within the sleeve (see Example 4), and thus increase the signal-to-noise ratio of the optical detection system. The amount of EMA glass may be changed to alter the ratio of open to solid area.

A spacer layer or outer cladding may be formed around the optical cladding and sleeve to appropriately space the apertures. The spacer layer may be formed of a relatively low temperature optical glass, which flows into the interstitial voids when the entire assembly is fused. The thickness of the spacer layer may be modified to change the center-to-center spacing of the holes, and the ratio of open to solid area.

In some embodiments, the fiber assembly may be both drawn and fused. An exemplary embodiment includes a plurality of 200-micron apertures, each of which includes the same internal sleeve, EMA ring, and outer cladding as described above. However, when drawn and fused, there may be no interstitial voids due to the fusion of the glass fibers.

Example 7

Exemplary Methods of Loading Samples/Reagents

This example describes methods for loading samples and/or reagents into a subdivided sample well or a subarray insert. An array-loading device may include a plurality of nozzles. Each nozzle may include a tip that extends into the interior of a sample compartment, that is, a sub-well or aperture, or each nozzle may mate by contact with an exterior surface of the subdivided sample well or subarray insert. The array-loading device may include an array of loading nozzles, with the array matching the spacing and positioning of sub-wells or apertures in the subdivided sample well or subarray insert. Each nozzle may widen at its distal portion to allow connection to a nozzle-specific reservoir. Thus, the entire nozzle array may taper towards the nozzle tips. Each reservoir may be loaded with a distinct sample and/or reagent. Aperture action, pressure exerted on the reservoir contents, or a vacuum exerted on the unmated side of a subarray insert (with apertures) may promote loading of sample or material into each sample compartment of an array. Loading may be carried out before or after placing a subarray insert into an array, such as that provided by the wells of a microplate.

Each nozzle also may have ports along the lateral cylindrical surface, instead of at the proximal end, such that by rotating the nozzle, specific portions of the interior surface, or individual rosette cavities, can be individually loaded or sampled. Similarly, a fiber optic bundle may be used to "read" assay results from individual interior surfaces or individual rosette cavities.

Example 8

Chemical Isolation of Sub-Wells

This example describes the results of several experiments that illustrate the chemical isolation of sub-wells in a superpositional array of wells.

The division of sample wells into sub-wells may provide several advantages over undivided wells, including an ability to hold sub-wells in and out of fluid isolation/communication with each other, as described previously. It therefore is desirable that there be no cross contamination between sub-wells, unless they are brought into fluid communication with each other by adding fluid reagent above the height of the sub-well walls. This example describes experimental results showing, using the embodiments described herein, that each sub-well remains effectively isolated from the other wells, so that there is little or no cross contamination between sub-wells loaded with sample materials (cells, for example) and empty sub-wells.

Experiments were performed using an array of machined sub-wells produced from a 1536-well microplate, as described above in Example 2. Some of the sub-wells were loaded with cells and adjacent sub-wells were left empty. No cross-contamination of the empty sub-wells with cells from adjacent sub-wells was observed, thus illustrating the fluid isolation of the individual sub-wells.

In other experiments, chemical isolation was tested using cell arrays. First, nine cell types were loaded into an array of nine sub-wells contained in each of two subdivided wells to form two positional cell arrays. Each subdivided well was treated with a different compound, with only one of the two compounds being toxic. In the well treated with the nontoxic compound, eight out of nine sub-wells contained live cells. By contrast, treatment with the toxic compound in the other wells killed every cell, so that no live cells were detected in any of the sub-wells. In both cases, there were no signs of cross-contamination between wells or sub-wells.

Similar results were obtained using a subarray insert having apertures to hold samples. Some of the apertures were loaded with fluorescently labeled cells and others were left empty. No cross contamination between loaded and empty wells was detected.

Example 9

Sub-Wells with Fluid-Control Structure

This example describes sub-well structures that may facilitate control of fluid entry into the sub-wells.

Adding the fluid to a subdivided well may produce significant turbulence within the sub-wells, especially for those sub-wells near a wall of the well or adjacent to a sub-well with a greater wall height. This may lead to uncontrolled mixing and other unwanted problems. At fluid deposition rates low enough to avoid this problem, samples in different sub-wells may be exposed to reagents for substantially different time periods, particularly for assays conducted over short time periods.

To minimize such problems, sub-wells may be configured to include a lip or ledge about the inside periphery near the top of each sub-well, at the mouth or fluid-entry point of the sub-well. The lip may be configured to narrow the sub-well near its top region but would leave an aperture through which materials and fluid are deposited, for example, via a pipet tip. Such sub-wells may be manufactured, for example, by injection molding followed by a heat press process. The lip may provide a horizontal flow diversion for fluid added above the height of the sub-wells, as well as a smaller cross section for fluid mixing. This may significantly restrict vertical fluid turbulence from entering the sub-wells.

The use of a lip or ledge in a sub-well at its mouth may have other advantages. By coating the opposing faces of the ledge (the inside face of the aperture) or the tops of the ledges with a hydrophobic material, the degree of control over adjustable fluid communication may be improved, as follows. Sub-wells may be filled to various heights via the mouth of each sub-well. Next, fluid may be deposited in the well region above the sub-wells. Due to the hydrophobic surface near each aperture, the deposited fluid may not enter any sub-well in which the fluid level in the sub-well is below the ledge, thereby forming an air bubble between the fluid in the sub-well and the fluid in the region of the well above the sub-well. Accordingly, plural wells may be addressed with fluid before there is fluid communication between the sub-wells and the overlying region of the well. In alternative embodiments, a ring about the interior surface near the top of the sub-well may be coated with a suitable hydrophobic material without the use of a lip or ledge on the sub-well. For example, in experiments performed with coatings, an allyl-silane coating on the sub-well top surface and top interior perimeter prevented aqueous liquid from entering the sub-well.

Vacuum may be used to initiate fluid communication between the sub-well fluid and the fluid placed in the well above the sub-well. The well, or more typically, a frame or microplate holding the well, may be briefly subjected a mild vacuum treatment to provide uniform mixing The mild vacuum draws the fluid-separating air bubbles out the sub-wells, and the evacuated space is replaced with the fluid in the well that overlies the sub-well, thereby generating a controlled direct fluid communication between the two fluids. Application of vacuum provides a "zero time point" for an experiment. Alternatively, it may be possible to accomplish the above using internal plumbing and valving.

Such controlled fluid communication may be used to add different amounts of reagent to different sub-wells. For example, different sub-wells may be addressed initially with fluid to different heights, and then fluid may be added to overlie all sub-wells as described above. However, when fluid communication is initiated, such as with the vacuum treatment described above, sub-wells filled to a lower level are infused with a larger volume, due to the larger air bubble that is displaced. Therefore, the initial concentration of reagent to which the sample is exposed can also be controlled in a sub-well-to-sub-well manner without additional pipeting to the sub-wells. Eventually, all the wells fully equilibrate with the reagent, but with a smaller aperture or mouth provided by a lip or ledge, this time may be significant. In any event, samples may be exposed to different initial concentrations of reagent and then assayed as the reagent concentration for the samples within the sub-wells is equalized.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A device for assaying a plurality of biological or chemical samples, comprising: a frame; and a plurality of wells disposed in the frame and addressable individually with fluid, each well including a plurality of sub-wells addressable with fluid either (a) individually, or (b) as two or more groups,
   wherein each well has an outer wall and at least two inner walls of lower height than the outer wall and different in height from each other, and wherein the at least two inner walls extend to different heights to form at least two levels, thereby dividing the well into the sub-wells and the two or more groups of sub-wells.

2. The device of claim 1, wherein each group is a linear array of sub-wells.

3. The device of claim 1, wherein the two or more groups are arrayed linearly within each well.

4. The device of claim 1, wherein a relatively low level of fluid over a sub-well disposes the sub-well in fluid isolation from the other sub-wells, wherein a relatively medium level of fluid over the sub-well disposes the sub-well in fluid communication with other sub-wells of only one of the two or more groups, and wherein a relatively high level of fluid over the sub-well disposes the plurality of sub-wells in fluid communication.

5. The device of claim 1, wherein the at least two inner walls include at least one higher wall dividing the well into rows or columns and at least one lower wall dividing the rows or columns into individual sub-wells.

6. The device of claim 1, wherein an insert defines the height of one or more of the inner walls of the sub-wells.

7. The device of claim 1, wherein the inner walls divide the well into groups of sub-wells disposed in rows or columns.

8. The device of claim 1, wherein the wells are arranged in rows and columns.

9. The device of claim 1, wherein each well is at least substantially rectangular in a horizontal plane.

10. The device of claim 1, wherein the frame, the plurality of wells, and the plurality of sub-wells are unitary.

11. A device for assaying a plurality of biological or chemical samples, comprising:

a frame;

a plurality of wells disposed in the frame and addressable individually with fluid;

a set of sub-wells disposed in each well and addressable individually or as a group by adjusting fluid levels, wherein the heights of the sub-wells are lower than that of said wells; and a set of relatively smaller sub-wells disposed in each sub-well and addressable individually or as a group by adjusting fluid levels, wherein the height of each relatively smaller sub-well is lower than that of said sub-wells.

\* \* \* \* \*